US00PP29586P3

(12) United States Plant Patent
Randag

(10) Patent No.: US PP29,586 P3
(45) Date of Patent: Aug. 7, 2018

(54) CALLA LILY PLANT NAMED 'MONTE CARLO'

(50) Latin Name: *Zantedeschia sprengeri*
Varietal Denomination: Monte Carlo

(71) Applicant: Sande B.V., 't Zand (NL)

(72) Inventor: Cecilius Jan-Jochem Randag, 't Zand (NL)

(73) Assignee: Dümmen Group B.V., De Lier (NL)

( * ) Notice: Subject to any disclaimer, the term of this patent is extended or adjusted under 35 U.S.C. 154(b) by 46 days.

(21) Appl. No.: 15/530,209

(22) Filed: Dec. 12, 2016

(65) Prior Publication Data

US 2017/0181359 P1 Jun. 22, 2017

Related U.S. Application Data

(60) Provisional application No. 62/386,953, filed on Dec. 17, 2015.

(51) Int. Cl.
*A01H 5/02* (2018.01)

(52) U.S. Cl.
USPC ..... Plt./490

(58) Field of Classification Search
USPC ..... Plt./263.1, 490
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

'Monte Carlo' is a new variety of calla lily having inflorescences with a yellow-colored spathe that produces 5-20 inflorescences per tuber. The inflorescence stems are about 22-50 cm in height, and the leaves are green with whitish spots and have a leathery texture.

4 Drawing Sheets

Botanical classification: *Zantedeschia sprengeri*.
Varietal denomination: 'MONTE CARLO'.

BACKGROUND OF THE NEW PLANT

The present invention comprises a new and distinct cultivar of calla lily, botanically known as *Zantedeschia sprengeri* and hereinafter referred to by the cultivar name 'Monte Carlo'.

'Monte Carlo' is a product of a planned breeding program which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as Z010161 (female parent, unpatented) with a *Zantedeschia sprengeri* selection referred to as Z030217 (male parent, unpatented). 'Monte Carlo' was selected in 2012 by the inventor in 't Zand, The Netherlands as one flowering plant within the progeny of the stated cross.

The first act of asexual reproduction of 'Monte Carlo' by tissue culture was performed by the inventor in September of 2012 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 18-20 cm pots at 12-14 weeks after planting in 't Zand, The Netherlands under greenhouse conditions, which approximate those generally used in horticultural practice. Color references are made to The 2001

R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Monte Carlo' which, in combination, distinguish this calla lily as a new and distinct cultivar:

1. Yellow-colored spathes;
2. Compact plant architecture;
3. High inflorescence production; and
4. Lanceolate-shaped leaves.

Further, when compared to calla lily plant named 'Yellow Jacket BLZ' (U.S. Plant Pat. No. 20,217), the upper surface spathe color of 'Yellow Jacket BLZ' is Yellow Group RHS 7A and the lower surface spathe color of 'Yellow Jacket BLZ' is Yellow Group RHS 7B, whereas the upper surface spathe color of 'Monte Carlo' varies between Yellow Group RHS 9A to 12A and the lower surface spathe color of 'Monte Carlo' varies between Yellow Group RHS 6A to 12A.

Table 1 provides differences of 'Monte Carlo' to its parents, *Zantedeschia sprengeri* selections Z010161 and Z030217.

TABLE 1

| 'Monte Carlo' | Differences | |
|---|---|---|
| Z010161 | Spathe color | Varies between White Group RHS N155C to Red-Purple Group RHS 62D |
| | Plant height | 25-50 cm |

TABLE 1-continued

| 'Monte Carlo' | Differences | |
|---|---|---|
| Z030217 | Spathe color | Varies between Green-Yellow Group RHS 1C to Yellow Group RHS 3A |
| | Plant height | 20-35 cm |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

The Plant

Figure 1:
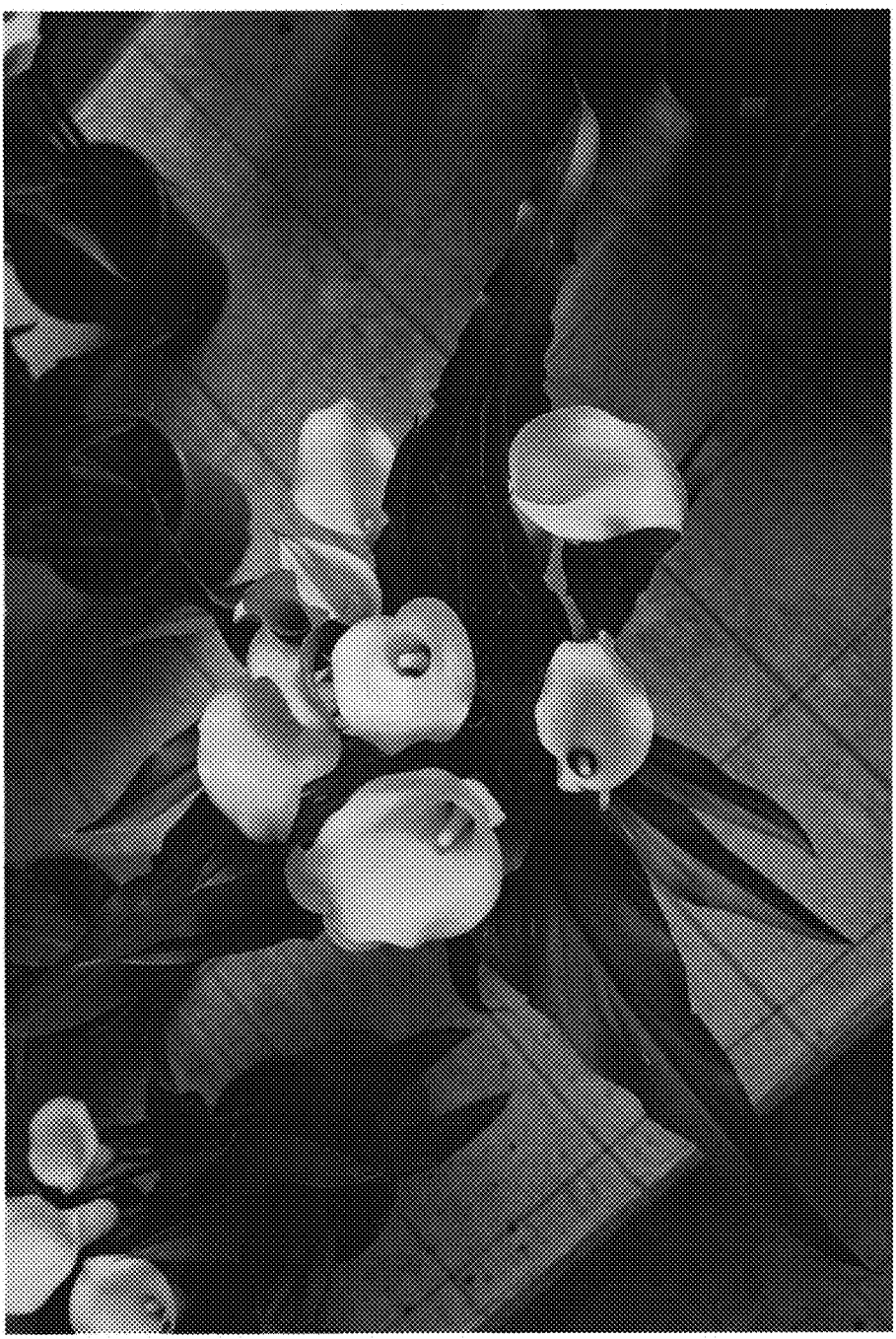
FIG. 1 is a photograph of an overhead view of the new variety.
Figure 2:
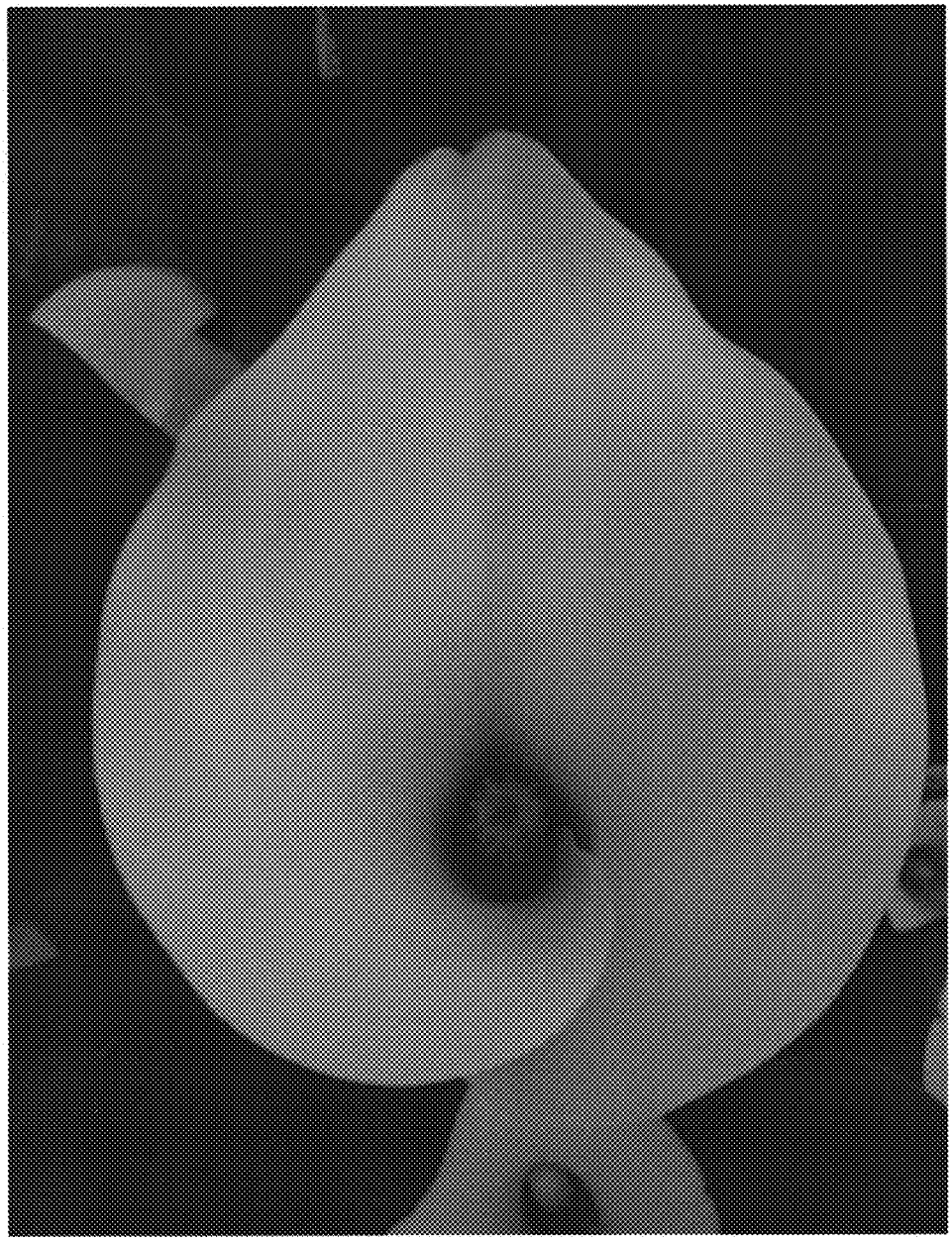
FIG. 2 is a photograph of a close-up view of the new variety.
Figure 3:
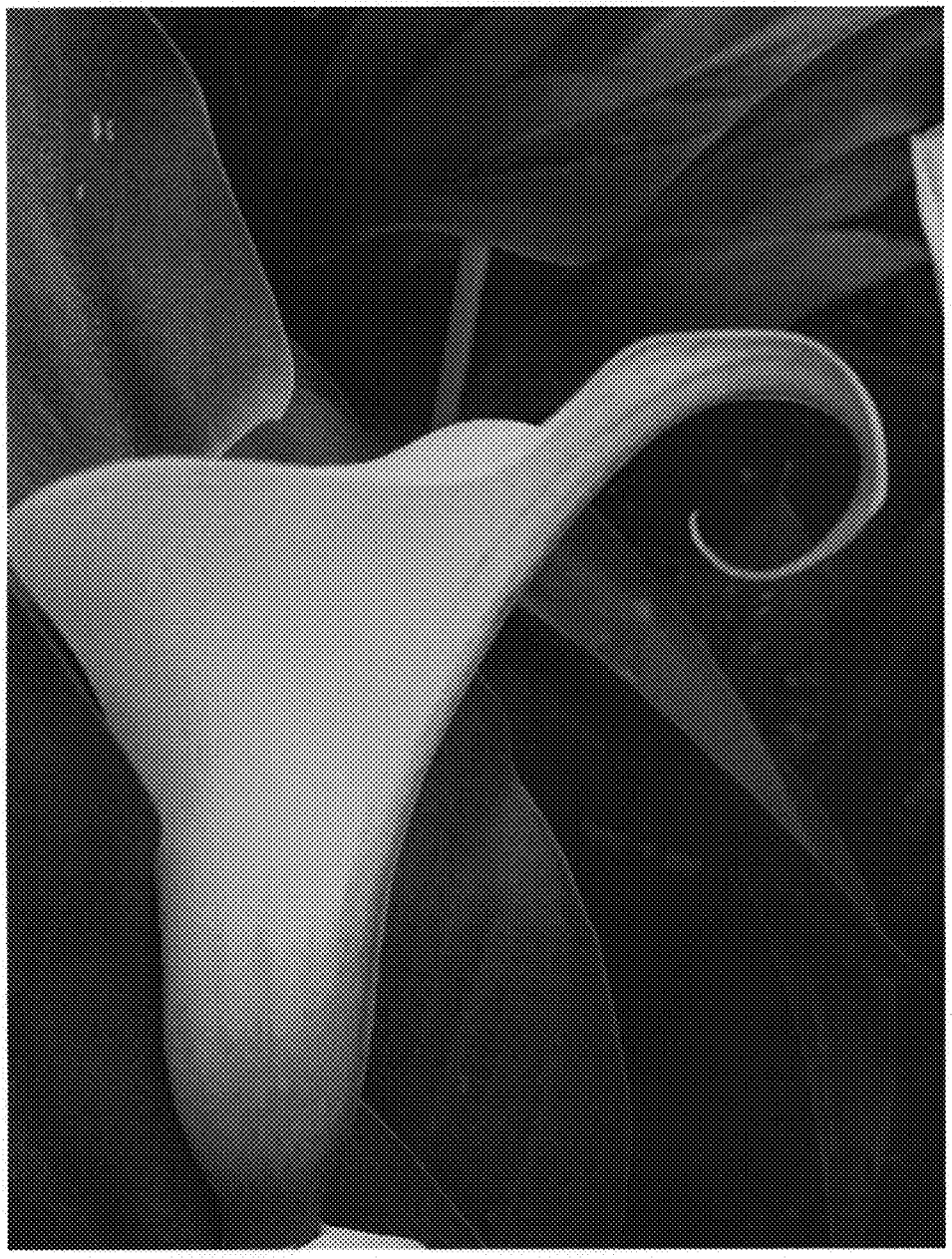
FIG. 3 is a photograph of a side view of the new variety.
Figure 4:
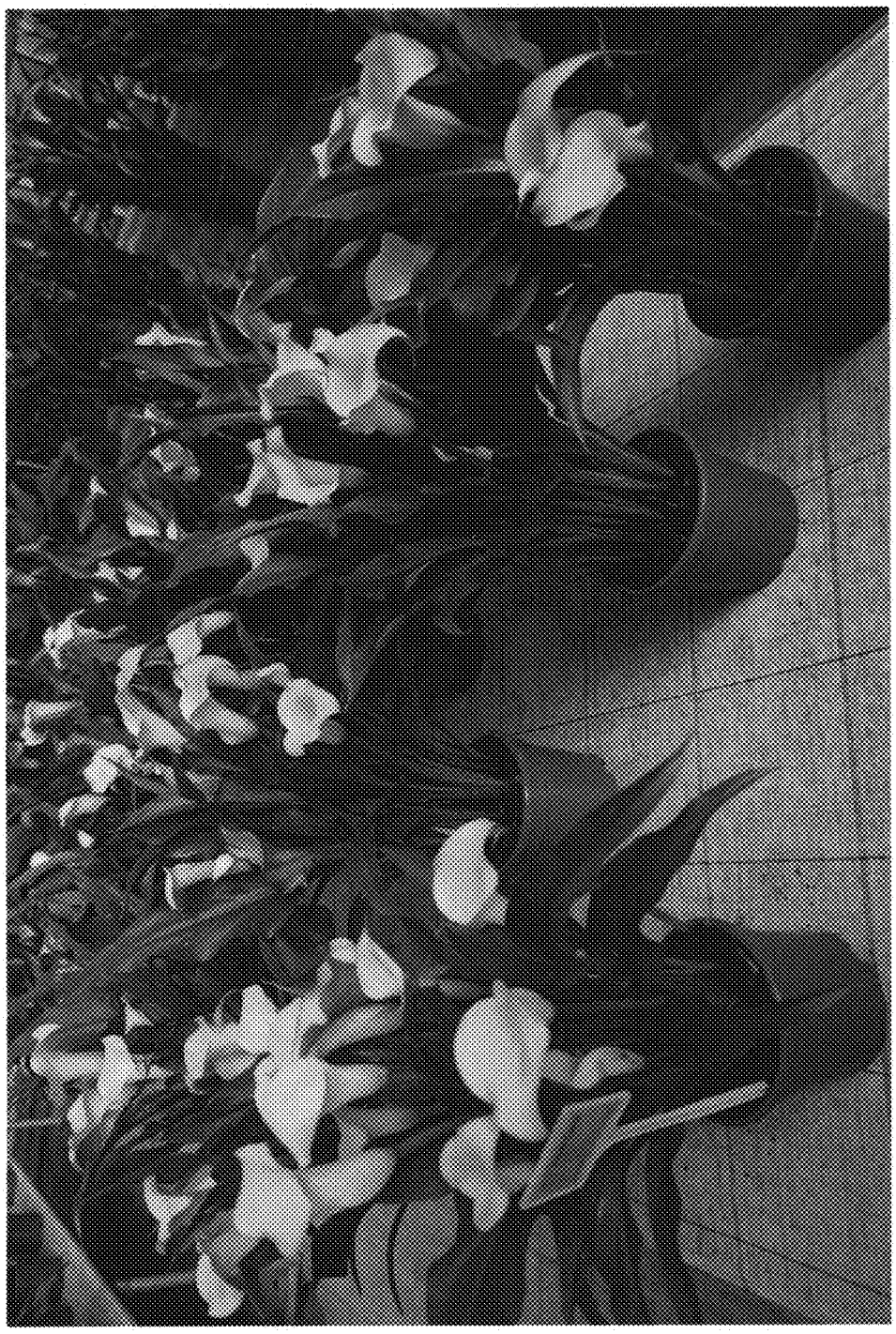
FIG. 4 is a photograph of a group of potted plants of the new variety.

Size:

*Height of the leaf canopy above the soil.*—15-44 cm.

*Height of top of inflorescence above the soil.*—20-50 cm.

*Diameter.*—6-12 cm.

Form: Erect.

Number of inflorescences per tuber:

*Size* 16-18 *cm in diameter.*—5-10 inflorescences.

*Size* 18-20 *cm in diameter.*—6-11 inflorescences.

*Size* 20-24 *cm in diameter.*—10-20 inflorescences.

Branches:

*Number.*—From 3-9.

*Color.*—Between Red-Purple Group RHS 59A to 60A.

Leaves:

*Size.*—Width: 2.5-11 cm. Length: 9.5-29 cm.

*Number per plant.*—14-25.

*Shape.*—Lanceolate.

*Color.*—Upper surface: Yellow-Green Group RHS 146A to 147A, with transparent White Group RHS 155A and N155A spots. Lower surface: Yellow-Green Group RHS 144A to 147A, with transparent White Group RHS 155A and N155A spots.

*Apex.*—Apiculate.

*Base.*—Attenuate.

*Margin.*—Undulate; having a color of Yellow-Green Group RHS 144A.

*Veins.*—Configuration: Pinnate. Color: Yellow-Green Group RHS 146A.

*Surface quality.*—Leathery.

*Petiole.*—Length: 2.5-24 cm. Average diameter: 10 mm. Color: The base is White Group RHS 155A and the upper part is Yellow-Green Group RHS 144A to Yellow-Green Group 146A.

Roots:

*Color.*—White.

*Branching.*—Similar to other *Zantedeschia* varieties.

The Inflorescence and Seeds

Spathe:

*Size.*—Length (measured from base opening to tip): 5.5-12 cm. Width: 3-6.5 cm. Height: 8-13 cm.

*Color.*—Upper surface: Varies between Yellow Group RHS 9A to 12A. Lower surface: Varies between Yellow Group RHS 6A to 12A.

*Vein color.*—Varies between Green Group RHS 143A to 143B in the middle, the remainder of the veins are transparent.

*Shape.*—Funnel.

*Apex.*—Apiculate.

*Base.*—Decurrent.

*Texture.*—Smooth (upper and lower surfaces).

Spadix:

*Size.*—Length: 22-45 mm. Diameter: 4-8 mm.

*Color.*—Between Yellow Group RHS 6A and 13A.

*Position relative to spathe.*—Upright.

Peduncle:

*Size.*—Length: 6-37 cm. Diameter: 3-13 mm.

*Color.*—The upper part is between Yellow-Green Group RHS 144A to 146A, and the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round. Length: Less than 1 mm. Color: Between Yellow Group RHS 6A and 13A.

*Filament.*—Length: Less than 1 mm. Color: Between White Group RHS 155A and 155B.

*Pistil.*—Number: 15 to 30. Length beyond perianth: About 1 mm.

*Stigma.*—Shape: Round. Size: Less than 1 mm.

*Style.*—Length: Less than 1 mm. Color: Between Yellow-Green Group RHS 154C and 154D.

*Ovaries.*—Texture: Smooth. Length: Between 1 to 10 mm. Width: Between 1 to 10 mm. Color: Top color is between Yellow Group RHS 6B and 9A, the bottom color is from White Group RHS 155B to Green-White Group RHS 157C.

Seeds:

*Length.*—4-7 mm.

*Width.*—3-6 mm.

*Color.*—Between Yellow-Green Group RHS 150A and 151A.

*Amount.*—Between 1-55.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Monte Carlo' as herein described and illustrated.

* * * * *